United States Patent [19]

Ackermann et al.

[11] 4,312,947

[45] Jan. 26, 1982

[54] PROCESS FOR THE PREPARATION OF A VACCINE AGAINST PANLEUCOPENIA OF THE CAT

[75] Inventors: Othmar Ackermann, Marburg; Helmut Stegmann, Rüchenbach, both of Fed. Rep. of Germany

[73] Assignee: Behringwerke Aktiengesellschaft, Marburg, Fed. Rep. of Germany

[21] Appl. No.: 761,438

[22] Filed: Jan. 21, 1977

[30] Foreign Application Priority Data

Jan. 23, 1976 [DE] Fed. Rep. of Germany ....... 2602478

[51] Int. Cl.³ .......................... C12N 7/08; C12N 7/00
[52] U.S. Cl. .................................. 435/237; 435/235
[58] Field of Search .......................... 424/89; 195/1.3; 435/235, 237

[56] References Cited

U.S. PATENT DOCUMENTS

| | | | |
|---|---|---|---|
| 3,293,130 | 12/1966 | Slater et al. | 195/1.3 |
| 3,520,972 | 7/1970 | Smith et al. | 195/1.3 |
| 3,892,627 | 7/1975 | Simons et al. | 195/1.3 |

*Primary Examiner*—Sam Rosen
*Attorney, Agent, or Firm*—Curtis, Morris & Safford

[57] ABSTRACT

A vaccine against panleucopenia is prepared by passing pathogenic panleucopenia virus first at least 80 times in cat kidney cells, then at least 18 times in permanent tissue cells of felidae or mustelidae, propagating the attenuated virus thus obtained on cat fetal cells and working it up to a vaccine.

9 Claims, No Drawings

PROCESS FOR THE PREPARATION OF A VACCINE AGAINST PANLEUCOPENIA OF THE CAT

This invention relates to a vaccine against feline distemper, also called infectious gastroenteritis or panleucopenia according to the main symptom, and to a process for the preparation of such a vaccine.

Feline or cat distemper is a virus disease specific for felidae. The pathogen, a parvo-virus, has the electron microscopic size of 20 to 25 nm. The virus is spread through the respiratory system and digestive system and it is discharged with the nasal secretion and the excrements. The disease starts after an incubation time of 2 to 6 days with refusal of food, fever, vomiting, in most cases diarrhea, with increasing infirmity and exsiccosis by loss of fluid. A highly developed panleucopenia appears. The mortality rate is up to 90%.

Cats which get over the disease are immunized. They can transmit antibodies to young cats via the colostrum. But after a while the young cats lose their protection as the maternal antibodies are gradually decomposed.

Cat distemper is spread all over the world, the organism causing the disease is highly infectious and pathogenic and thus cats are strongly exposed.

Attempts have been made to prepare an attenuated virus suitable for the manufacture of a virus vaccine cat distemper by passages in tissus cultures. However, a minimum of 6 passages and even 10 to 30 passages are not sufficient to obtain a stable attenuated virus which can serve as the active principle of vaccines, because the inoculated virus is discharged and taken up by other cats and by these animal passages remutations may occur.

It has also been proposed to propagate attenuated panleucopenia virus in feline embryo tissue. Because only small amounts of tissue can be obtained from feline embryos, this method is little practicable for economic reasons.

The present invention provides a process for the preparation of a vaccine against panleucopenia which comprises passing pathogenic panleucopenia virus first at least 80 times in feline kidney cells, then at least 18 times in permanent tissue cells of felidae or mustelidae, propagating the attenuated virus obtained in cat fetal cells and working up the virus to obtain a vaccine. Other objects of this invention are to provide an attenuated panleucopenia virus, a process for preparing such an attenuated virus and a vaccine against panleucopenia containing the attenuated virus.

The first step of attenuation, which preferably comprises 80 to 100 passages, takes place in cell cultures of cat kidneys cultivated in nutrient media commonly used for cell reproduction. The cells can be cultivated as a cell monolayer or as a cell suspension. For cultivating, a temperature in the range of from 35° to 39° C., preferably 36.5° to 37.5° C. should be maintained. A culture of this type should be infected early, at the latest when the cells have grown about 75%. As the infection medium, the supernatant of the preceding infected cell culture is used. It is added to the cell culture in a ratio of 1:5 to 1:20. Two to six days after the infection the supernatant can be separated and transferred to the following cell culture.

After 80 to 100 passages in the manner described above, the virus-containing supernatant is transferred to a permanent tissue culture of felidae or mustelidae. Permanent cultures to be used are described in the literature. There is mentioned, by way of example, the Crandell cell, i.e. a permanent cat kidney cell. This cell culture is inoculated with the supernatant of an infected culture and worked up in the manner described above.

The virus is attenuated to a sufficient degree after at least 18 passages in permanent tissue cells. It is then completely apathogenic, innocuous and well tolerated. The immunogenicity of the virus is not reduced by the attenuation and the vaccines prepared therewith have excellent immunizing properties.

The attenuated virus, characterized by the scientific name of "panleucopenia virus strain BW 103", is on deposit at the Institute for Hygienics and Epidemiology at Prague, Czechoslovakia, under the number CNTCCAO 3/77.

The virus attenuated in this manner can be propagated in tissue cultures of cat fetuses. Especially suitable are fetuses obtained in the stage of organogenesis, approximately in the last third of the gestation period. For the preparation of tissue cultures the entire fetuses or parts thereof may be used. It is recommended not to use the extremities, the head and the skin for the cell culture. The cells are worked up in usual manner, for example they are trypsinized as a stationary culture, as a roller culture or as a suspension culture, and inoculated with the attenuated virus as described above for propagation. The supernatant is harvested after 2 to 6 days. The infected cell cultures can be further cultivated with the addition of fresh nutrient medium. This operation can be repeated several times, for example in the case of a stationary culture at least 4 to 6 times, and with a roller culture at least 20 to 25 times. Thereafter, the cells are generally exhausted. In the last working up, the cells can be disaggregated, for example by deep freezing or ultrasonic treatment, to obtain a higher yield.

The material obtained by working up the propagation culture can be treated in usual manner to obtain the vaccine. Suitably, a stabilizer, for example gelatin, meat extract, peptone, or sugar solution, is added, especially when the vaccine is to be lyophilized, which is recommended for a better stability. It is likewise possible, however, to use the vaccine as a liquid vaccine. If desired, the usual adjuvants can be added.

In the case of a lyophilized vaccine, it is dissolved in a usual solvent and administered subcutaneously or intramuscularly. As compared to known vaccine it is distinguished by the following advantages;

(1) high purity of the antigens
(2) because of propagation on homologous tissue no reaction due to foreign protein; no shock or allergies in repeated administration
(3) uniform quality and purity of the inocculated virus due to the propagation on a uniform tested cell substratum
(4) rapid protection.

The panleucopenia virus vaccine in accordance with the invention was extensively tested in the laboratory and in animal experiments as to its properties, tolerability, innocuousness and efficiency.

Test and Results

Innocuousness

To test the innocuousness of the vaccine, white mice and guinea pigs were used. 5 mice were vaccinated subcutaneously with 0.5 ml each of redissolved vaccine. 2 guinea pigs were vaccinated intraperitoneally with 2 ml each. During the observation period of 10 days the test animals remained healthy. Special importance was attached to innocuousness and tolerance tests in cats. In controlled laboratory and outdoor tests, 962 mainly isolated cats and 174 great cats such as lions, tigers and hunting leopards, were vaccinated subcutaneously and intramuscularly with the vaccine of the invention and generally the animals were observed for 14 days and in part for several weeks. Besides the observation of local and general reactions, in the laboratory test also the leucocytes were counted. The vaccine was well tolerated. The vaccination of SPF cats (SPF=free from specific pathogen), in part isolated for more than 2 years, did not give rise to any objection either.

Stability

A uniformly good efficiency of the vaccine of the invention depends not only on the virus titer but also on the stability of the vaccine. To test the stability, the content of virus in the vaccine was determined after storage at different temperatures for a period of up to 24 months after production. The antigen titers obtained are summarized in the following Table 1.

TABLE 1

Stability test of the vaccine after storage at different temperatues, (starting titer after preparation = $10^{4.833} ID_{50}/ml$)

| Storage time | virus content in $ID_{50}$ at storage temperatures of | | | | |
|---|---|---|---|---|---|
| | +37° C. | +20° C. | +10° C. | +4° C. | -35° C. |
| 1 week | $10^{3.833}$ | | | | |
| 3 weeks | $10^{3.375}$ | | | | |
| 1 month | $10^{3.375}$ | $10^{4.166}$ | | | |
| 2 months | $10^{1.50}$ | $10^{4.375}$ | | | |
| 3 months | $10^{1.375}$ | $10^{4.375}$ | $10^{4.833}$ | $10^{4.835}$ | |
| 4 months | no virus | $10^{4.166}$ | | | |
| 6 months | | $10^{3.50}$ | $10^{4.833}$ | $10^{4.625}$ | $10^{4.833}$ |
| 9 months | | $10^{3.50}$ | 10 | | |
| 12 months | | $10^{3.5}$ | $10^{4.625}$ | $10^{4.833}$ | $10^{4.833}$ |
| 18 months | | $10^{2.625}$ | $10^{4.625}$ | $10^{4.833}$ | $10^{4.833}$ |
| 24 months | | $10^{2.625}$ | $10^{4.5}$ | $10^{4.833}$ | $10^{4.833}$ |

Efficiency and tolerance

In addition to the determination of the content of living virus in the cell culture by virus titration, the vaccine of the invention was tested in a series of immunization experiments with cats. Because of the wide distribution of the panleucopenia virus and other felid-specific pathogens, cats were bought and kept in quarantine before carrying out the tests. In order to avoid foreign infections and to obtain accurate test results, it proved advisable to use cats free from specific pathogen, so-called SPF cats.

Animal experiment No. 1

In this first experiment the efficiency and tolerance of the vaccine was tested in 6 SPF cats. 4 of the cats, which were all kept in isolation, were vaccinated subcutaneously with the vaccine. The other 2 remained unvaccinated for control purposes. Besides an examination of the general conditions of health, the leucocytes were counted after administration of the vaccine to find out whether their number significantly decreased as compared with the unvaccinated cats, which was not the case in the present and in further experiments. The efficiency was tested serologically by measuring the antibodies and by subsequent challenges with virus. The result of this experiment is listed in Table 2. It can be seen that prior to vaccination the cats were susceptible to panleucopenia and that 2 weeks later the vaccinated cats were serologically immune and withstood challenge, whereas the control cats had no protection and died from the disease.

TABLE 2

Examination of the vaccine as to its efficiency in SFF cats

| Cat no. | PL-antibody titer prior to vaccination | vaccinated with | clinical de- velopement up to 14 d.p.v | PL-Antibody titer $ND_{50}/ml$ 14 d.p.v. | challenge infection | result |
|---|---|---|---|---|---|---|
| 59 | 0 | 1 ml of vaccine | NAD | 681 | 1 ml per | NAD |
| 62 | 0 | of invention | NAD | 1.466 | | NAD |
| 65 | 0 | subcutaneously | NAD | 1.466 | kg body | NAD |
| 67 | 0 | | NAD | 3.162 | weight | NAD |
| 61 | 0 | control | NAD | 0 | pathogenic PL- virus | signs of disease * |
| 64 | 0 | | NAD | 0 | perorally | signs of disease | d.p.v. = days post vaccination
NAD = no abnormality discovered
* = died of panluekopenia
PL = panleukopenia
$ND_{50}$ = 50% neutralizing final value

Animal experiment No. 2

Vaccines containing live apathogenic panleucopenia virus generally ensure a rapid protection which can be attributed in the first place to the phenomenon of interference, according to which the pathogenic virus is prevented from propagating in the host cell by the inoculated virus. A test with 12 kittens was carried out to find whether they were sufficiently protected against a challenge infection 72 hours after administration of the vaccine of the invention. The test results are listed in Table 3. It can be seen that the vaccine ensured a protection against panleucopenia after a short period of time, i.e. within 3 days. Prior to vaccination, all kittens had no protection. 3 Days later the vaccinated kittens withstood a challenge infection with pathogenic panleucopenia virus. After the infection, the leucocytes were counted daily over a period of 14 days. The kittens exhibited no signs of the disease and the number of leucocytes did not decrease to a significant extent. The starting values and the minimum values found during the test are summarized in Table 3. A decrease of leucocytes below $2,000/mm^3$ is generally considered a characteristic sign of panleucopenia. The unvaccinated control kittens showed more or less severe signs of panleucopenia and 4 of 6 animals died.

TABLE 3

Efficiency test of the vaccine 72 hours after vaccination (p.v.)

| Kitten no. | PL-antibody prior to vaccination | vaccinated with | challenge 72 hrs. p.v. | Result general state of health | leucocytes up to 2 weeks p.v. starting value | minimum value |
|---|---|---|---|---|---|---|
| 268 | 0 |  |  | NAD | 13,400 | 10,200 mm$^3$ |
| 596 | 0 | 1 ml each | 1 ml | NAD | 20,000 | 10,600 mm$^3$ |
| 599 | 0 | of vaccine of inven- | = 100 ID$_{50}$ | NAD | 12,100 | 5,600 mm$^3$ |
| 602 | 0 | tion sub- | per kg of | NAD | 14,600 | 10,300 mm$^3$ |
| 604 | 0 | cutaneous- ly | body weight of panleu- cope- | NAD | 11,300 | 10,100 mm$^3$ |
| 606 | 0 |  | nia PL- | NAD | 18,800 | 10,200 mm$^3$ |
| 269 | 0 |  | virus | SOD | 11,400 | 600 mm$^3$* |
| 600 | 0 |  | No. 1 | SOD | 10,100 | 5,700 mm$^3$* |
| 601 | 0 | controls | peroral- | SOD | 13,200 | 1,200 mm$^3$* |
| 605 | 0 |  | ly | SOD | 12,300 | 1,200 mm$^3$* |
| 603 | 0 |  |  | SOD | 10,600 | 4,200 mm$^3$* |
| 607 | 0 |  |  | SOD | 15,800 | 3,800 mm$^3$ |

NAD = no abnormality developed;
SOD = Signs of disease
* = died of panleukopenia
ID$_{50}$ = 50% infecting dose

Animal experiment No. 3

Animal experiment No. 2 demonstrates that the vaccine prepared in accordance with the invention protected cats against panleucopenia (PL) already 3 days after vaccination (3 d.p.v.). The present experiment was carried out to find out whether the vaccine affords protection against PL earlier than 3 days after vaccination.

16 Cats susceptible to panleucopenia were vaccinated with one dose each of the vaccine and divided into 4 groups of 4 animals each. One group was challenged with pathogenic panleucopenia virus directly after vaccination and the other groups succesively at intervals of one day each. Six unvaccinated control cats were infected with the last group at the third day after vaccination. The results indicated in Table 4 show that some of the vaccinated cats had acquired protection against panleucopenia even one day after vaccination. Only one animal of the respective group of 4 cats showed signs of panleucopenia and died, while the other three remained free from the disease.

Of the group challenged two days after vaccination the number of leucocytes of one animal only decreased slightly on the fourth and fifth day after infection to 4,200 and 5,100/mm$^3$. All cats of the group infected three days after vaccination resisted the challenge without any reaction.

All control cats died of panleucopenia. Further details are indicated in Table 4.

TABLE 4

Efficiency test 0, 1, 2, and 3 days after vaccination

| Cat No. | PL-antibodies in ND$_{50}$/ml a.v. | vaccinated on Nov. 26 with | | challenge infection | |
|---|---|---|---|---|---|
| 1017 | 0 | 1 ml each | on Nov. 26 | 1 ml each PL- | + 7. d.p.i. |
| 1022 | 32 | of vaccine |  | infected material, | + 12. d.p.i. |
| 1028 | 0 | subcutaneously | 0 d.p.v. | No. 1 diluted | + 8. d.p.i. |
| 1166 | 0 |  |  | 1:5 per kg of | + 10 |
| 1018 | 0 |  | on Nov. 27 | body weight per os | NAD |
| 1023 | 0 |  |  |  | NAD |
| 1029 | 0 |  | 1 d.p.v. |  | + 9. d.p.i. |
| 1167 | 0 |  |  |  | NAD |
| 1019 | 0 |  | on Nov. 28 |  | NAD |
| 1024 | 0 |  |  |  | NAD |
| 1160 | 0 |  | 2 d.p.v. |  | L(4.200)4.d.p.i. |
| 1168 | 0 |  |  |  | NAD |
| 1020 | 0 |  | on Nov. 29 |  | NAD |
| 1025 | 0 |  |  |  | NAD |
| 1165 | 0 |  | 3 d.p.v. |  | NAD |
| 1169 | 0 |  |  |  | NAD |
| 1021 | 0 | control | on Nov. 29 |  | + 6. d.p.i. |
| 1031 | 0 | animals |  |  | + 6. d.p.i. |
| 1158 | 0 |  |  |  | + 6. d.p.i. |
| 1159 | 0 |  |  |  | + 6. d.p.i. |
| 1163 | 7 |  |  |  | + 6. d.p.i. |
| 1164 | 0 |  |  |  | + 8. d.p.i. | a.v. = ante vaccinationem
d.p.v. = days post vaccinationem
+ = died of PL
L = decrease of leucocytes
NAD = no abnormality developed
(...) = lowest leucocyte value
d.p.i. = days post infectionem

Animal experiment No. 4

To determine the duration of protection a further test was carried out with SPF cats kept in strict isolation. 8 of 10 SPF cats were vaccinated subcutaneously with one dose each of the vaccine. To control the excretion and to prevent a possible spreading of the vaccine virus or an introduction of panleucopenia virus, the 2 unvaccinated cats were kept in the same room. All cats were bled to measure the antibodies. The results are indicated in Table 5. It can be seen that the vaccine ensured an active immunity with a high titer of antibodies conferring upon the vaccinated cats a reliable protection against panleucopenia over the whole period of observation. It can also be seen that the control cats remained free from antibodies. This means that during the running of the test, the vaccine virus was not spread and panleucopenia virus was not introduced, which would have caused a natural boost or a break out of panleucopenia in the control cats with subsequent development of antibodies. The cats of the experiment were looked after daily so that it could be ascertained that during the entire test period no reactions occured which would point to incompatibility reactions or toxicity.

10% of Eagle's Medium (10-fold)
10% of sheep or calf serum
2% lactalbumin hydrolysate (of 5% (w/v) strength)
1% of NPS solution (Neomycin-Streptomycin-Penicillin 20,000 μg/ml or 20.000 I.U/ml)
2% of sodium bicarbonate (of 5% (w/v) strength) the balance to 100% being double distilled water.

The mixture was introduced into a culture flask and maintained at 37° C.

The nutrient medium was renewed on the second, fourth and seventh day. On the tenth day the nutrient medium was separated from the cells by decantation and replaced by a solution containing 95% of a trypsinizing medium, 1% of a 1% (w/v) solution of disodium dihydrogen ethylenediaminetetraacetate, 1% of a 1% (w/v) trypsin solution and 3% of a 5% (w/v) sodium bicarbonate solution.

The trypsinizing medium contained
1 liter of double distilled water
7.27 g of sodium chloride

TABLE 5

Examination of duration of protection in SPF cats after vaccination

| Cat No. | vaccinated with | titer of panleucopenia antibodies $ND_{50}$/ml | | | | | | |
|---|---|---|---|---|---|---|---|---|
| | | prior to vaccination | 2 weeks p.v. | 1 month p.v. | 2 months p.v. | 4 months p.v. | 6 months p.v. | 8 months p.v. |
| 151 | 1 ml each | 0 | 4,217 | 6,813 | 4,210 | 6,813 | 3,162 | 6,813 |
| 152 | of vaccine | 0 | 3,162 | 3,162 | 6,813 | 3,162 | 3,162 | 3,162 |
| 154 | of invention sub- | 0 | 3,162 | 6,813 | 1,466 | 4,217 | 1,466 | * |
| 155 | | 0 | 4,217 | 14,660 | 6,813 | 3,162 | 2,371 | 4,217 |
| 156 | cutane- | 0 | 4,217 | 4,217 | 4,217 | 3,162 | 2,371 | 3,162 |
| 157 | ously | 0 | 3,162 | 6,813 | 4,217 | 3,162 | 3,162 | 4,217 |
| 158 | | 0 | 3,162 | 6,813 | 14,660 | 4,217 | 6,813 | 4,217 |
| 159 | | 0 | 14,660 | 23,710 | 23,710 | 4,217 | 2,371 | 6,162 |
| 153 | control | 0 | 0 | 0 | 0 | 0 | 0 | 0 |
| 160 | cats | 0 | 0 | 0 | 0 | 0 | 0 | 0 | p.v. = post vaccination
* = died during heart puncture

| Cat No. | 11 months p.v. | 14 months p.v. | 17 months p.v. | 23 months p.v. | 26 months p.v. |
|---|---|---|---|---|---|
| 151 | 3,162 | 422 | 2,371 | 1,466 | 6,813 |
| 152 | 3,162 | 1,466 | 3,162 | 3,162 | 3,162 |
| 154 | | | | | |
| 155 | 4,217 | 316 | 422 | 1,466 | 4,217 |
| 156 | 3,162 | 1,466 | 1,466 | 3,162 | 3,162 |
| 157 | 3,162 | 2,371 | 3,162 | 6,813 | 6,813 |
| 158 | 14,660 | 3,162 | 3,162 | 6,813 | 6,813 |
| 159 | 6,813 | 2,371 | 4,217 | 4,217 | 6,813 |
| 153 | 0 | 0 | 0 | 0 | 0 |
| 160 | 0 | 0 | 0 | * | 0 |

* = died during the experiment

The following example illustrate the invention. All percentages if not otherwise stated are by volume.

EXAMPLE (1) Preparation of a culture of cat fetal cells

A pregnant cat was killed without pain and the fetuses were removed under sterile conditions. The head, the ends of the extremities and the skin were removed from one fetus and the remaining body was cut with a pair of scissors into pieces about 2 to 4 mm in size.

The pieces were introduced into a 0.25% (w/v) trypsin solution and heated to 37° C. while stirring. At intervals of about 10 to 20 minutes, the trypsin solution containing suspended cells was decanted and replaced by fresh trypsin solution.

6 ml of the decanted cell sediment were suspended in a ratio of 1:300 parts by volume in a medium having the following composition:

0.36 g of potassium chloride
0.91 g of dextrose.

In this solution the cell agglomerates disintegrated into single cells or smaller groups. The cells obtained in this manner were repeatedly cultivated in the manner described above.

(2) Preparation of panleucopenia seed virus

A cat was infected with pathogenic panleucopenia virus obtained from a cat suffering from and which died of panleucopenia and after 7 days it was killed with severe signs of the disease and a leucocyte count of 200/mm³. The kidneys of the cat were removed and treated as described above in a 25% (w/v) trypsin solution to obtain a cell suspension. The virus suspension obtained was subjected to sedimentation and the sediment suspended in ratio of 1:300 in a culture medium having the following composition:
52.2% of Hanks' Medium
5.8% of lactalbumin hydrolysate 20.0% of Tissue Culture Medium 199
20.0% of calf serum
1.0% of sodium bicarbonate (of 5% strength)
1.0% NSP solution The suspension was maintained at 37° C. to cause propagation of the panleucopenia virus in the cells. The virus could be detected by administration of the culture supernatant to healthy cats.

The virus was further cultivated under the following conditions: The kidneys of healthy cats were removed, trypsinized as described above and suspended in nutrient medium. When the monolayer of the cells had grown by about 75%, it was inoculated with the virus-containing supernatant of the panleucopenia virus culture.

To this end the supernatant was mixed with fresh nutrient medium in a ratio of 1:10 by volume and disposed in a layer above the cells. After 4 days, the supernatant containing the propagated panleucopenia virus was poured off. After about 80 repetitions of this procedure, the used kidney cells were replaced by a permanent cat kidney cell strain according to Crandell and the passages were repeated another 17 times.

To cultivate stable cat kidney cells the following medium was used:
10% Eagle's Medium
10% calf serum
1.5% sodium bicarbonate solution (5% strength)
1.0% NSP solution, the balance to 100% being double distilled water.

For virus inoculation the proportion of serum was reduced to 3%.

After the 103rd passage, the virus had lost its pathogenity but conserved its good immunizing properties. It can be used for the preparation of a vaccine against panleucopenia.

(3) Preparation of the vaccine

A culture of cat fetal cells propagated as described sub (1) was suspended in a medium composed of
10% of Eagle's Medium (10 fold)
10% of calf serum
2% of lactalbumin hydrolysate (5% (w/v) strength)
2% of sodium bicarbonate (5% (w/v) strength)
1% of NSP solution
75% of double distilled water After 1 to 2 days, the nutrient solution was replaced by fresh nutrient solution. When the monolayer of cells had grown by 50 to 75%, a 10% virus suspension obtained as described sub (2) was pipetted on to the cell culture.

After 4 days, the virus-containing supernatant was decanted and the cell culture further cultivated with the addition of fresh nutrient solution. The supernatant had a virus titer of about $10^5$ $ID_{50}$/ml. The virus-containing supernatant was worked up in known manner to a vaccine by adding a stabilizer consisting of
4 parts of gelatin broth (2% (w/v) strength)
1 part of glucose (50% (w/v) strength)

The vaccine was filled in portions of 1 ml each into small 3 ml bottles with a beaded neck, lyophilized and sealed under reduced pressure.

The virus can also be propagated in the manner described above in roller or suspension cultures.

What is claimed is:

1. Attenuated apathogenic panleucopenia virus strain Bw 103.

2. A method for making an attenuated panleucopenia virus, which method comprises first passing pathogenic panleucopenia virus at least 80 times in cat kidney cells and then at least 18 times in a permanent cat kidney cell strain according to Crandell.

3. A method as in claim 2 wherein said attenuated virus is subsequently propagated in cultures of cat fetal cells.

4. A method as in claim 3 wherein said cultures of cat fetal cells are harvested several times.

5. A method as in claim 2 wherein said attenuated virus is subsequently propagated in stationary cultures of cat fetal cells and said cultures are harvested at least 4 to 6 times.

6. A method as in claim 2 wherein said attenuated virus is subsequently propagated in roller cultures of cat fetal cells and said cultures are harvested at least 20 to 25 times.

7. At attenuated apathogenic panleucopenia virus prepared according to the method of claim 3.

8. A method for making a vaccine against panleucopenia of felidae, which method comprises combining an effective amount of an attenuated panleucopenia virus as in claim 7 with a vaccine adjuvant or carrier.

9. A vaccine against panleucopenia of felidae, said vaccine containing an effective amount of an attenuated panleucopenia virus as in claim 7 in combination with a vaccine adjuvant or carrier.

* * * * *